US005614197A

United States Patent [19]

Pathak et al.

[11] Patent Number: 5,614,197
[45] Date of Patent: Mar. 25, 1997

[54] POLYPODIUM EXTRACT AS PHOTOPROTECTANT

[75] Inventors: Madhukar A. Pathak, Belmont; Salvador Gonzalez, Boston; Thomas B. Fitzpatrick, Weston, all of Mass.

[73] Assignee: Industrial Farmaceutica Cantabria, S.A., Madrid, Spain

[21] Appl. No.: 388,261

[22] Filed: Feb. 13, 1995

[51] Int. Cl.$^6$ ............................ A61K 35/78; A61K 7/42; A61K 7/44
[52] U.S. Cl. ............................ 424/195.1; 424/59; 424/60
[58] Field of Search .................................. 424/195.1, 60, 424/59

[56] References Cited

U.S. PATENT DOCUMENTS

| | | | |
|---|---|---|---|
| 4,206,222 | 6/1980 | Valetas et al. | 514/460 |
| 5,145,675 | 9/1992 | Won | 424/78.31 |
| 5,256,404 | 10/1993 | Martino et al. | 424/59 |
| 5,306,486 | 4/1994 | McCook et al. | 424/59 |

FOREIGN PATENT DOCUMENTS

| | | | |
|---|---|---|---|
| 0503208A1 | 9/1992 | European Pat. Off. | A61K 35/78 |
| 2024662 | 1/1980 | United Kingdom . | |
| 2075834 | 11/1981 | United Kingdom . | |
| WO90/03778 | 4/1990 | WIPO | A61K 7/00 |

OTHER PUBLICATIONS

Alvarez, X.A. et al., Effects of Anapsos on Behavior and Brain Cytokines in Rats, Annals of Psychiatry 3:329–341 (1992).
Beauchamp C., and I. Fridovich, Superoxide Dismutase: Improved Assays and an Assay Applicable to Acrylamide Gels, Anal. Biochem. 44:276–287 (1971).
Carraro C., and M. Pathak, Studies on the Nature of In Vitro and In Vivo Photosensitization Reactions By Psoralens and Porphyrins J. Invest. Dermatol. 90:267–275 (1988).
Corrales Padilla, H. et al., A new agent (hydrophilic fraction of polypodium leucotomos) for management of psoriasis, Int. J. Dermatol. 13(5):276–282 (1974).
Fernandez, D. et al., Immunosupressive and pharmacologically active compounds from polypodium leucotomos L., Book of Abstracts: First World Cong. Medicinal and Aromatic Plants for Human Welfare, Maastricht, Netherlands, Poster 84 (1992).
Horvath, A. et al., Metabolic Effects of Calagualine, an Antitumoral Saponine of Polypodium leucotomos, Nature 214:1256–1258 (1967).
Jimenez, D. et al., Anapsos, an antipsoriatic drug, in atopic dermatitis, Allergol. et Immunopathol. 15(4):185–189 (1987).
Kraljic I. and S. Mohsni, A new method for the detection of singlet oxygen in aqueous solutions, Photochem. Photobiol. 28:577–581 (1978).
Pathak, M.A., Topical and Systemic Approaches for the Prevention of Acute and Chronic Sun–Induced Skin Reactions, Dermatologic Clinics 4(2):321–334 (1986).
Pathak, M.A., Topical and Systemic Photoprotection of Human Skin Against Solar Radiation, Clinical Photomedicine, H.W. Lim and N.A. Soter, (eds.), New York, Marcel Dekker, Inc., 1993, 287–306.
Pathak M., and T. Fitzpatrick, Preventive Treatment of Sunburn, Dermatoheliosis, and Skin Cancer with Sun–Protective Agents, Dermatology in General Medicine, 4th Ed., T. Fitzpatrick, et al. (eds.), New York, McGraw–Hill, 1994, 1689–1717.
Rayward, J. et al., Polypodium leucotomos (PL), an herbal extract, inhibits the proliferative response of T. lymphocytes to polyclonal mitogens, Second Intl. Cong. on Biol. Response Modifiers, San Diego, USA (1993).
Tuominen, M. et al., Enhancing Effect of Extract Polypodium Leucotomos on the Prevention of Rejection on Skin Transplants, Phytotherapy Research 5:234–237 (1991).
Tuominen, M. et al., Effects of calaguala and an active principle, adenosine, on platelet activating factor, Planta Med. 58:306–310 (1992), 306–310.
Vargas, J. et al., Anapsos, an antipsoriatic drug which increases the proportion of suppressor cells in human peripheral blood, Ann. Immunol. (Inst. Pasteur) 134(C):393–400, 1983.
Package insert, and English translation thereof, for the product DIFUR®, Industrial Farmacéutica Cantabria, S.A., Madrid, Spain.
Package insert, and English translation thereof, for the product ARMAYA®, Laboratorios Centrum, S.A., Alicante, Spain.
Package insert, and English translation thereof, for the product REGENDER®, Laboratorio Alacan, S.A., Alicante, Spain.
Padilla, H. et al., The use of oral and topical polypodium leucotomus (DIFUR®) in the therapy of vitiligo, Meeting of the American Academy of Dermatology, San Francisco, Jul. 1994, poster presentation.
Gonzalez, S. et al., Polypodium leucotomos extract as an antioxidant agent in the therapy of skin disorders, SID Abstract vol. 102(4), Apr. 1994, Poster presentation No. 763.
Alomar, A. et al., Extracto de polypodium leucotomos (PL) como terapeutica en el vitiligo, 23rd Congreso Nacional de Dermatologia y venereologia, Madrid, Jun. 1994, Poster presentation No. 450.
Copy of the International Search Report.
J. Investigat. Dermatol. 102(4):651 (Apr. 1994) (Abstract–S, Gonzales et al).
Dermatology Clinics, 4(2):321–334 (Apr. 1986).

(List continued on next page.)

Primary Examiner—John W. Rollins

[57] ABSTRACT

The invention provides new methods and products for use in photoprotection from ultraviolet radiation. The products include extracts from ferns of the genus Polypodium mixed in prepartions for topical application and oral administration. The preparations have both photoprotective and antioxidant properties. The topical formulations may also include physical and/or chemical sunscreen agents and/or cosmetic agents.

29 Claims, 3 Drawing Sheets

OTHER PUBLICATIONS

Jaen P. et al., Empleo potencial del extracto de polypodium leucotomus en el tratamiento delvitiligo, 23rd Congreso Nacional de Dermatologia y venereologia, Madrid, Jun. 1994, Poster presentation No. 457.

Gonzalez S. et al., Implicacion del polypodium leucotomos en la preservacion de las celulas de langerhans epidermicas tras exposicion a radiacion ultravioleta B., 23rd Congreso Nacional de Dermatologia y venereologia, Madrid, Jun. 1994, Poster presentation No. 458.

Gonzalez S. et al., Extracto de polypodium leucotomos (DIFUR®) antioxidante natural frente al estres fotooxidativo, 23rd Congreso Nacional de Dermatologia y venereologia, Madrid, Jun. 1994, Poster presentation No. 459.

GENERATION OF SUPEROXIDE ANION BY RIBOFLAVIN AND UVA AS A FUNCTION OF UVA EXPOSURE DOSE AND THE SCAVENGING OF SUPEROXIDE ANION PRODUCTION BY PLE

GENERATION OF SUPEROXIDE ANION BY RIBOFLAVIN AND UVB AS A FUNCTION OF UVB EXPOSURE DOSE AND THE SCAVENGING OF SUPEROXIDE ANION PRODUCTION BY PLE

PRODUCTION OF SINGLET OXYGEN BY ROSE BENGAL (RB $10^{-5}$M) AS A FUNCTION OF UVA DOSE AND THE EFFECT OF PLE ON THE GENERATION OF SINGLET OXYGEN

POLYPODIUM EXTRACT AS PHOTOPROTECTANT

FIELD OF THE INVENTION

The present invention relates generally to the field of dermatology and, in particular, to providing photoprotection and antioxidant protection to the skin. The invention further particularly relates to providing protection from ultraviolet radiation from the sun or artificial sources.

BACKGROUND OF THE INVENTION

Although the exposure of individuals to moderate sunlight has many beneficial effects, including the synthesis of vitamin D and the killing of certain pathogens, over-exposure of human skin to sunlight and, in particular, to the ultraviolet band of the spectrum, has many deleterious effects, including sunburn, phototoxicity, photoallergic reactions, photoaging, and the promotion of skin cancers. As a result of concerns about the deleterious effects of over-exposure to sunlight, much research has been directed to the development of both topical and systemic photoprotective agents and preparations for use in cosmetics and sunscreens (for reviews, see M. A. Pathak, *Dermatologic Clinics* 4(2):321–334 (1986); M. A. Pathak, "Topical and Systemic Photoprotection of Human Skin Against Solar Radiation," in H. W. Lim and N. A. Sotek, (eds.), *Clinical Photomedicine*, New York, Marcel Dekker, Inc. (1993); M. A. Pathak and T. B. Fitzpatrick, "Preventive Treatment of Sunburn, Dermatoheliosis, and Skin Cancer with Sun-Protective Agents," in Fitzpatrick, T. B., et al., (eds.), *Dermatology in General Medicine*, 4th Edition, New York, McGraw-Hill, (1994)).

In general, topical photoprotective preparations "sunscreens" can be categorized as chemical, physical, mixed. Topical chemical sunscreen preparations are usually translucent preparations that contain one or more ultraviolet-absorbing compounds. Topical physical sunscreen preparations are usually opaque or semi-opaque preparations that contain compounds that do not necessarily absorb ultraviolet radiation but, rather, reflect or scatter radiation UV because of their opacity and particle size (30–100 nm). Topical mixed sunscreen preparations contain a mixture of chemical and physical sunscreen agents. Topical sunscreen preparations are generally formulated as solutions (in, e.g., alcohol; alcohol plus glycerol or propylene glycol), or as lotions, creams and ointments (e.g. oil-in-water or water-in-oil emulsions). In addition, topical sunscreens preparations may be included in cosmetic preparations along with cosmetic agents such as pigments, perfumes, and the like.

Although many agents have been suggested as possibly providing systemic photoprotection after oral administration, evidence of their effectiveness remains largely anecdotal or inferential (see M. A. Pathak and T. B. Fitzpatrick (1994), supra). Even the mechanisms by which many of these agents may work is speculative, ranging from optical filtration and epidermal thickening to the inhibition of membrane-lipid peroxidation and protection of DNA from photodamage.

Polypodium is a genus of plants typical of the fern family, Polypodiaceae. In 1967, Horvath et al. reported that an extract or infusion of one species of fern, *Polypodium leucotomos*, traditionally used by the natives of northern Honduras as a treatment for malignant tumors, had been shown both in vitro and in vivo to have antitumoral effects (A. Horvath, et al., *Nature* 214:1256–1258 (1967)). Since then, extracts from a variety of fern plants, some referred to as Polypodium extracts and some referred to as calagualine, have been found to have a number of dermatological, immunomodulatory and behavioral effects.

Extracts of *Polypodium leucotomos* have been found effective in the treatment of psoriasis, atopic dermatitis and other skin disorders (see, e.g., H. Corrales Padilla, et al., *Int. J. Dermatol.* 13(5):276–282 (1974); D. Jimenez, et al., *Allergol. et Immunopathol.* 15(4):185–189 (1987)). In these settings, the extract was found to cause decreases in hyperkeratosis, parakeratosis, epidermal mitosis, epidermal thickening, epidermal prolongations, and the severity and extent of epidermal lesions.

Processes for producing polar extracts of the ferns *Dryopteris crassirhizoma, polypodium vulgare*, Linn, *Polypodium leucotomos, Phlebodium decumanum*, J. Smith, *Polypodium decumanum, Cyathea taiwaniana*, or rhizomes of *Polypodium aureum*, Linn., and *Polypodium triseriales* were disclosed in GB Patent 2,024,622A to Ramon, et al. (filed May 24, 1979). This patent also claimed medicaments prepared from such extracts and suggested their oral use in the treatment of psoriasis and parapsoriasis.

Similarly, processes for producing polar extracts from a variety of ferns of the family Polypodiaceae were disclosed in GB Patent 2,075,834A to Ramon et al. (filed Mar. 26, 1981). This patent suggested the oral use of such extracts in the treatment of osteolocomotive diseases (e.g., arthritis).

U.S. Pat. No. 4,206,222 to Valetas (issued Jun. 3, 1980) also discloses a method of producing extracts from a variety of ferns in the Polypodiaceae family. In addition, Valetas claims an active agent of a particular chemical structure, a $C_8$ delta-lactone, isolated from these ferns. The active agent is disclosed to be useful in the treatment of collagen diseases (e.g. arthritis).

Extracts of *Polypodium leucotomos* also have been found to increase the number of T8 lymphocytes, to decrease the T4/T8 ratio in blood, to prolong the survival of skin allografts in mice, to inhibit the proliferative response of mouse spleen cells, and to inhibit the proliferative response of T lymphocytes to mitogens (see, e.g., J. Vargas, et al., *Ann. Immunol. (Inst. Pasteur)* 134(C):393–400 (1983); D. Jimenez, et al., *Allergol. et Immunopathol.* 15(4):185–189 (1987); M. Tuominen, et al., *Phytother. Res.* 5:234–236 (1991); D. Fernandez, et al., *Book of Abstracts: First World Cong. Medicinal and Aromatic Plants for Human Welfare*, Maastricht, Netherlands, Poster 84 (1992); J. Rayward, et al., *Second Int. Cong. on Biol. Response Modifiers*, San Diego, USA (1993)).

X. A. Alvafez, et al. tested the effects of a Polypodium extract on the behavior and brain cytokines of rats. Their data indicated that the extract induces hypokinesia at moderate-high doses, with no effect on psychomotor habituation, in an open-field psychomotor activity test; improves learning in a passive avoidance behavior test; decreases levels of the cytokines IL-1$\beta$ and IL-2 in frontoparietal cortices; decreases IL-1$\beta$ in the hippocampus; and increases TNF-$\alpha$ in the cortex (X. A. Alvarez, et al., *Annals of Psychiatry* 3:329–341 (1992)).

In another study, extracts of *Polypodium decumanum* ("Calaguala") were shown to inhibit the release of the proteolytic enzyme elastase in human neutrophils induced by platelet activating factor (PAF) and to inhibit the biosynthesis of PAF (M. Tuominen, et al., *Planta Med.* 58:306–310 (1992)). Because PAF may be involved in the pathogenesis of psoriasis, the authors of this study speculated that the anti-PAF activity of the extract may contribute to its clinical efficacy in the treatment of psoriasis.

Prior to the present invention, however, the photoprotective and antioxidant properties of topically applied and systemically administered Polypodium extract for normal skin were unknown. Thus too, prior to the present invention, methods of providing photoprotection and antioxidant protection by topical application or systemic administration of Polypodium extracts were unknown.

SUMMARY OF THE INVENTION

Preparations including extracts of ferns of the genus Polypodium are provided. In particular, the extracts may be from any of the ferns *Polypodium aureum, Polypodium crassifolium, Polypodium decumanum, Polypodium lanceolatum, Polypodium leucotomos, Polypodium percussum, Polypodium triseriale,* or *Polypodium vulgare*. The preparations may be formulated for topical application or oral administration.

For topical application, the preparations include a pharmaceutically acceptable carrier for topical application. In addition, the topical preparations may include physical sunscreen agents, chemical sunscreen agents and/or cosmetic agents. In particular, a physical sunscreen agent such as titanium dioxide, silicone-treated titanium dioxide, zinc oxide, ferrous oxide, ferric chloride, talc, chromium oxide, or cobalt oxides may be included. Alternatively or in addition, a chemical sunscreen agent such as para-amino benzoic acid, esters of para-amino benzoic acid, salicylates, cinnamates, benzophenones, dihydroxyacetone, parsol 1789, or melanin may be included. The preparations may contain at least 1%, 10%, 25%, or 50% Polypodium extract by weight. In addition, the preparations may provide a sun protection factor (SPF) for the minimal erythematic dose (MED) evaluated at 24 hours of at least 2, 5, 10 or 15 when applied at 2 $\mu$l/cm$^2$ to normal skin of Types I to Type IV. A packaged product for topical application, including instructions for use, is also provided. Using the products of the invention, methods of providing photoprotection to an individual with normal skin also are provided.

For oral administration, the preparations include a pharmaceutically acceptable carrier for oral application. A packaged product for oral administration, including instructions for use, is also provided. Using the products of the invention, methods of providing photoprotection to an individual with normal skin also are provided. These methods include orally administering to an adult a dosage of a Polypodium extract between 720 mg and 1440 mg within a 24 hour period prior to exposure to ultraviolet radiation, and orally administering a dosage of between 360 mg and 720 mg within a 3 hour period prior to exposure.

DETAILED DESCRIPTION OF THE INVENTION

Figure 1:
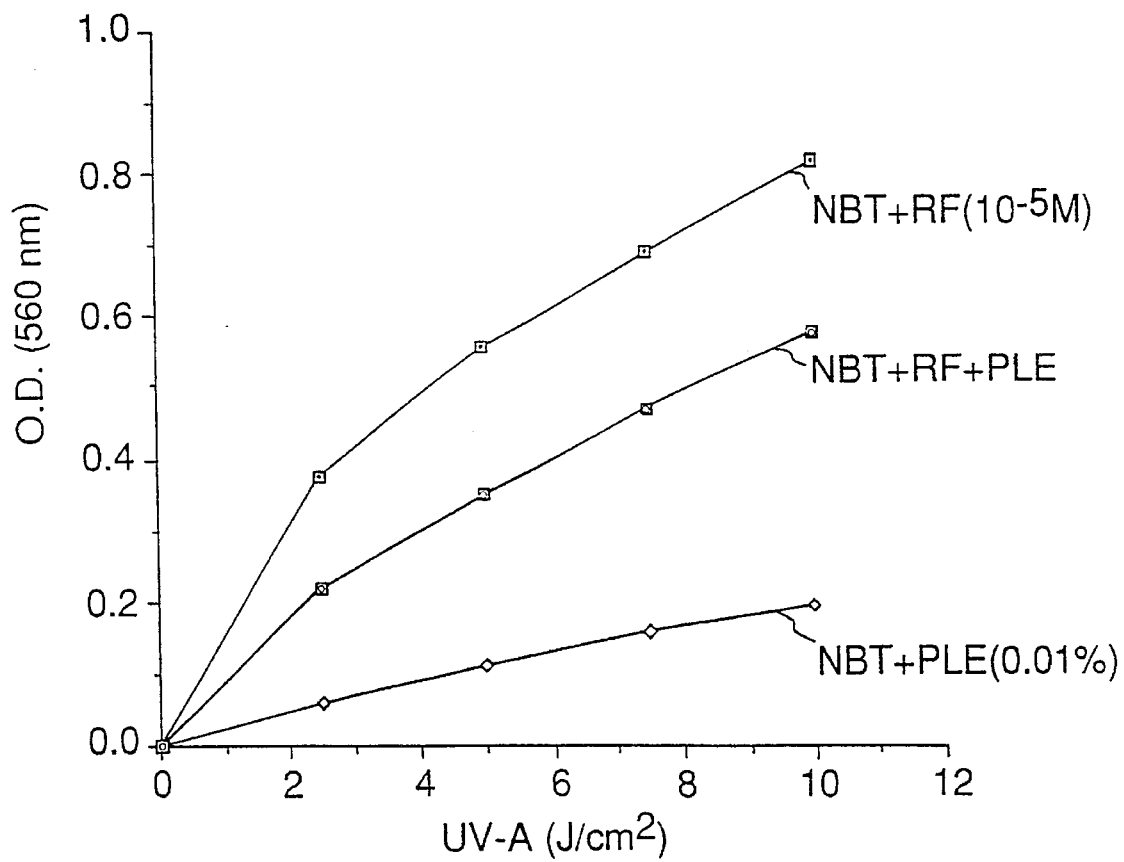
FIG. 1 plots the generation of superoxide anion as a function of UVA dose. Superoxide anion generation is measured by changes in optical density at 560 nm resulting from the conversion of NBT to NBF by reaction with superoxide anion. Riboflavin (RF) was used as a photosensitizer. From top to bottom, the three graphs show the superoxide anion generation by RF alone, by RF in the presence of Polypodium extract (PE), and by PE alone.

The present invention is directed to the use of extracts of fern plants of the genus Polypodium for photoprotection and antioxidant protection. The present invention is also directed to photoprotective and antioxidant preparations including such extracts. In one set of embodiments, the methods and preparations are directed only to topical use of the extracts, whereas in another set of embodiments, the extracts may be administered systemically.

I. Polypodium Extracts

The Polypodium extracts of the prior art and the present invention are hydrosoluble or hydrophilic extracts which may be produced by standard alcohol or polar extractions of the dried leaves and/or rhizomes of ferns of the genus Polypodium. The polar extraction may be preceded or followed by a non-polar or lipid separation, and then the polar extract may be filtered and concentrated. Additional steps may be added to remove pigments and cations. General protocols for producing polar extracts for the Polypodiaceae may be found in GB 2,024,622A and GB 2,075,834A. In addition, protocols for producing two *Polypodium leucotomos* extracts (one ethanolic and one methanolic) are presented in Tuominen, et al., *Phytotherapy Research* 5:234–236 (1991). Another and preferred method of extraction is provided in Example 1 below.

Extracts of one Polypodium species, *Polypodium leucotomos*, are already commercially available in Spain, Portugal, Honduras and the Dominican Republic in the form of capsules for oral administration. The preferred commercial preparation for oral administration is from Industrial Farmacéutica Cantabria, S. A., Madrid, Spain (DIFUR®).

As used hereafter, the term "Polypodium extract" and the abbreviation "PE" shall mean a polar (or hydrosoluble or hydrophilic or hydroalcoholic) fraction extracted from the leaves and/or rhizomes of a fern of the genus Polypodium and having photoprotective and antioxidant properties.

Ferns in this genus include *Polypodium leucotomos* (also known as *Polypodium aureum* and *Phlebodium aureum*) described in the *Index Londinensis*, Vol. 5, Oxford, 1921; *Polypodium decumanum* (also known as *Phlebodium multiseriale* and *Chrysopteris dictyocallis*) described in *Ann. Bot.*, Vol. 31, 1917; *Polypodium crassifolium* (also known as *Dipteris crassifolia* and *Polypodium enocarpum*) described in *Species Plantarum,* Stockholm, 1753–63; *Polypodium lanceolatum* described in the *Index Londinensis,* Vol. 5, Oxford, 1921; *Polypodium percussum* described in the *Index Londinensis,* Vol. 5, Oxford, 1921; *Polypodium triseriale* described in the *Index Filicum,* Copenhagen, 1906; and *Polypodium vulgare* described in the *Index Londinensis,* Vol. 5, Oxford, 1921. Of these, the preferred fern for producing the extract of the present invention is *Polypodium leucotomos.*

As described in Example 1, and only as an example, such extracts may be obtained by ethanolic or methanolic extraction of Polypodium leaves and/or rhizomes. In preferred embodiments, only the aerial portions of the plant are used. Other hydrophilic solvents may, of course, be used in place of ethanol or methanol (e.g., water, lower alkyl alcohols). A hydrophobic extraction or "defatting" step may also be used to remove hydrophobic or lipidic components from the polar extract. As will be understood by one of ordinary skill in the art, such a hydrophobic or lipid extraction may be employed either before or after the polar or hydrophilic extraction. Similarly, multiple extractions may be performed to further refine the polar or hydrophilic fraction. Indeed, as will be understood by one of ordinary skill in the art, a variety of fractionation and separation techniques (e.g., chromatography, dialysis, filtration, electrophoresis) may be employed in various orders and multiplicities to further refine the polar extract and to isolate the active ingredient(s). At each step of such fractionation or separation, one may, without undue experimentation, perform the simple antioxidant assays described in Examples 6 and/or 7 to determine which fraction contains the active ingredient of PE. Any such polar or hydrophilic fraction of an extract derived from the leaves and/or rhizomes of Polypodium and having photoprotective and antioxidant properties constitutes a "Polypodium extract" or "PE" as used herein and in the appended claims.

After evaporation of volatile solvents, such extracts are typically syrupy in consistency and amber to brown in color (but may be clarified by means of activated charcoal). Both the consistency and color, of course, will vary depending upon the degree to which the extract is diluted with water or other solvents.

For purposes of quantifying the amount of PE in a preparation, and for purposes of definiteness in the appended claims, it is necessary to recognize that a PE may be concentrated or dilute and, therefore, a greater quantity of dilute extract will be needed to achieve the same utility as any given quantity of concentrated extract. A preparation containing, comprising or including x % PE by weight, therefore, is defined as a preparation in which the Polypodium extract, if concentrated, would constitute x % by weight. A concentrated Polypodium extract shall be defined as one losing no more than 25% of its weight upon drying.

II. The Photoprotective Properties of PE

Ultraviolet radiation is subdivided into three bands from the longer to the shorter wavelengths. These three bands are referred to as UVA, UVB, and UVC. The UVC region includes wavelengths less than approximately 290 nm but, due to filtering by ozone in the upper atmosphere, is largely absent at the surface of the earth. The UVB region extends from approximately 290–320 nm and the UVA region extends from approximately 320–400 nm.

The effects of ultraviolet radiation on human skin are several. Therefore, the effectiveness of a composition as a photoprotectant may be evaluated by several different criteria. Among these are the following.

(1) Determination of the absorption spectrum of the composition. If the absorption spectrum of a composition shows specific absorption in the ultraviolet band from 290–400 nm, and particularly with peak absorption at 290–320 nm, the composition may be considered as a photoprotectant against sunburn reaction (which is usually caused by 290–320 nm solar radiation).

(2) Determination of the minimum dose of solar radiation needed to induce immediate pigment darkening with and without application/administration of the composition. The immediate pigment darkening (IPD) reaction can be induced by long wave ultraviolet radiation (320–400 nm). The reaction, which is most noticeable in light brown or tanned skin, is a transient darkening of the skin that becomes apparent upon termination of UVA exposure. It results from an oxidation reaction of preexisting melanin in the skin. The IPD reaction can be inhibited by antioxidants or, because the reaction requires oxygen, by depriving the skin of oxygen. The minimum dose of UVA radiation that produces a visible darkening of the skin can be determined by exposing the skin to graded doses of UVA radiation ranging from 0.5 to 10 $J/cm^2$. The lowest dose of UVA radiation that produces visible darkening of the skin immediately after irradiation is scored as the minimum dose for IPD.

(3) Determination of the minimal erythematic dose with and without application/administration of the composition. The minimal erythematic dose (MED) is defined as the minimal dose of ultraviolet radiation of 290–320 nm that produces perceptible sunburn reaction in human skin with detectable boundaries at 20–24 hrs after exposure. The MED may be determined by exposing the skin to graded doses of UVB radiation. The MED ranges from approximately 20 to 80 $mJ/cm^2$ of UVB radiation for fair-skinned individuals and from approximately 70–120 $mJ/cm^2$ in brown or darkly pigmented persons. It should be noted that MED values vary with the wavelengths of the ultraviolet spectrum. Shorter wavelength (290–320 nm) radiation is 500 to 1000 times more erythematic than longer wavelength (320–400 nm). Therefore, MEDs for longer wavelength radiation are higher (e.g., 20 to 50 $J/cm^2$).

(4) Determination of the minimal melanogenic dose with and without application/administration of the composition. The minimal melanogenic dose (MMD) is defined as the minimal dose of ultraviolet radiation (UVB or UVA) that produces persistent or lasting pigmentation of the skin that is visible 72 to 120 hrs after exposure and does not fade soon thereafter. If the skin is examined microscopically, the pigment cells show increased population density (melanocytes per $cm^2$), increased dendritic processes, and increased levels of melanin pigmentation. The MMD may be determined by exposing the skin to graded doses of ultraviolet radiation (290–400 nm) and noting the lowest dose that induces persistent pigmentation.

(5) Determination of the minimal phototoxic dose with and without application/administration of the composition. In the determination of MED, it is known that shorter wavelength (290–320 nm) radiation is more erythemogenic than longer wavelength (320–400 nm) radiation. However, in the presence of a photoreactive chemical or drug (e.g., 8-methoxypsoralen, 5-methoxypsoralen), the longer wave UVA radiation can become much more erythemogenic. This is due to a phototoxic reaction in which the skin shows redness (erythema) at a much reduced dose of UVA radiation. The minimal dose of UVA radiation required to produce phototoxic reaction after application/administration of a photoreactive chemical or drug is defined as the minimal phototoxic dose (MPD). The MPD may be determined by topically applying or orally administering a photoreactive chemical or drug prior to exposing the skin to graded doses of UVA radiation and noting the lowest dose that induces a phototoxic reaction 48 to 72 hrs after exposure.

As used herein, the term "photoprotection" means (1) the inhibition or retardation of erythema or sunburn reaction and tissue damage to skin and/or (2) the inhibition or retardation of the immediate pigment darkening reaction and/or (3) the inhibition or retardation of the delayed tanning or MMD reaction and/or (4) the inhibition or retardation of phototoxic reaction produced by psoralens. A compound providing such photoprotection is said to be "photoprotective" and may be referred to as a "photoprotectant."

For commercial products, the effectiveness of a photoprotective preparation is usually expressed as its "sun protection factor" (SPF). The SPF is defined in terms of the MED of protected and unprotected skin according to the following equation:

$$SPF = \frac{MED \; (mJ/cm^2) \; of \; sunscreen \; protected \; skin}{MED \; (mJ/cm^2) \; of \; untreated \; (control) \; skin}$$

The U.S. Food and Drug Administration sets standards for the determination of SPFs. The standards require the application of test products at 2 µl/cm² or 2 mg/cm² on the back (infrascapular region) of the test subjects. A 100 cm² skin area (50×2 cm) is selected for the evaluation of each test product. A standard sunscreen (8% homosalate) is used as an internal standard to verify the test results.

By analogy to the SPF defined above, one can also define a "Protection Factor" for the IPD and the MMD. As with the SPF, these protection factors are simply ratios of the minimum doses needed for protected skin to the minimum doses needed for unprotected skin.

The degree of sun protection needed depends, of course, not only on the dosage of radiation but also on the individual's type of skin. In general, normal human skin can be classified into sun-reactive Types I-VI (Type I being the lightest and most sensitive and Type VI the darkest and least sensitive) based in large part upon the degree of constitutive melanization and the facultative capacity of the skin to darken or tan in response to ultraviolet radiation. For a discussion of these skin types, see M. A. Pathak, *Annals New York Academy of Sciences*, 453:328-339 (1985), incorporated herein by reference.

As used herein, the term "normal skin" means human skin which is not photosensitized and which is free of dermatological conditions such as psoriasis, atopic dermatitis, and vitiligo. As used herein, the term "photosensitized" means made more susceptible to photodamage by ingestion or topical application of a compound such as a psoralen.

To assess the photoprotective properties of PE, a variety of experiments were performed using topical and oral formulations of PE and using subjects with normal skin which was either treated or untreated with skin photosensitizing agents. The details of these experiments are provided in Examples 2–5 below.

For topical application of PE, four different formulations were tested. The formulations each consisted of concentrated PE mixed into a lotion as described in Example 8. The different formulations from each other (and from the lotion of Example 8) only in the percentage by weight of PE in the formulation. For each formulation, 200 µl was applied either once or twice to 100 cm² of skin surface as indicated:

"10%": 10% PE applied once

"25%": 25% PE applied once

"50% 1×"": 50% PE applied once

"50% 2×"": 50% PE applied twice

For oral administration, dosages of up to 720 mg per day were tested (total dosages ranging from 1440 mg over two days to 3600 mg over 5 days) using commercially available PE capsules (DIFUR®, Industrial Farmacéutica Cantabria, S.A., Madrid, Spain).

These experiments have demonstrated the following in individuals with Type III or IV skin:

(1) Depending upon the concentration, PE topically applied to normal skin showed a protection factor for the IPD reaction of between 2.20 and 3.55, showed a protection factor (SPF) for the MED of at least 2.35 to greater than 3.00, and showed a protection factor for the MMD of at least 1.96 to greater than 2.23. See Example 2.

(2) PE orally administered to patients with normal skin acts as a systemic photoprotectant and, depending upon the dosage, showed a protection factor for the IPD reaction of between 2.70 and 3.09, showed a protection factor (SPF) for the MED of between 2.65 and 2.94, and showed a protection factor for the MMD of between 1.67 and 2.00. See Example 3.

(3) PE topically applied to skin photosensitized by oral psoralens showed a protection factor for the MPD evaluated at 72 hrs which, depending on the concentration of PE, was greater than 1.5 to greater than 2.2 with oral 5-MOP or which, even at the lowest concentration, was greater than 4.0 with oral 8-MOP. See Example 4.

(4) PE orally administered to subjects with skin photosensitized by psoralens showed a protection factor for the MPD measured at 72 hrs ranging from 3.0 (with oral 5-MOP) to 7.0 (with oral 8-MOP). See Example 5.

III. The Antioxidant Properties of PE

The fact that PE not only retards the phototoxic reaction to psoralens and UVA ("PUVA," see Examples 4 and 5) but also retards the IPD reaction suggests that its mechanism of action may involve the quenching of free radicals and reactive oxygen species. It is known that free radicals and reactive oxygen species play an important role in causing various degrees of cellular damage and in perpetuating inflammatory response (erythema, edema, vesiculation) to psoralens (Carraro and Pathak, *J. Invest. Dermatol.* 90:267–275, (1988)). These studies indicated that (1) psoralens interact with the DNA of epidermal cells to produce photoadducts with the pyrimidine bases (including single-stranded and cross-linked photoadducts), and (2) psoralens produce reactive oxygen species, including singlet oxygen, superoxide anion and hydroxyl radical, that contribute to epidermal cell membrane damage, lipid peroxidation and the development of the inflammatory response. Similarly, the available evidence, based on action spectra studies, indicate the existence of two distinct mechanisms of action of UVR, depending upon the wavelengths and the nature of UV radiation damage: (1) A shorter wavelength mechanism involving UVB radiation (290–320 nm) that operates through direct absorption of photons by DNA and results in damage to DNA in the form of DNA base photoproducts (e.g., cyclobutylpyrimidine dimers and 6–4 pyrimidine-pyrimidone photoproducts of cytosine); (2) A longer wavelength UV mechanism that operates through non-DNA intermediates such as reactive oxygen species ($^1O_2$, $O_2^{\cdot-}$, and $\cdot OH$ etc.) that are produced through either endogenous sensitizers (e.g., NADH, NADPH, riboflavin, quinones, etc.) or exogenous sensitizers (e.g., psoralens+UVA). The longer wavelengths also contribute to inflammation and other oxidative stress reactions that cause damage to DNA, membrane lipids, and cytoplasmic organelles. The most reactive free radical is the hydroxyl radical ($\cdot OH$) resulting from the generation of superoxide anion ($O_2^{\cdot-}$). Both singlet oxygen ($^1O_2$) and $O_2^{\cdot-}$ can cause membrane lipid peroxidation, DNA damage and cross linking of proteins in the epidermis as well as the dermis.

In order to test the free radical quenching or antioxidant properties of PE, a series of in vitro experiments were performed involving photosensitization reactions by UVA/UVB and riboflavin and by UVA and rose bengal. These experiments indicate that:

(1) PE (0.01%) decreased $O_2^{\cdot-}$ production by UVA and riboflavin and by UVB and riboflavin by 42.2% and 55%, respectively (see Example 6).

(2) PE (0 01%) decreased $^1O_2$ production by UVA and a known photosensitizer (see Example 7).

Although currently available PE does not show any characteristic absorption peaks in the UVB or UVA regions, a crude extract exhibited monotonically increasing absorption values in these regions. Thus, PE appears to act in two ways: (a) as a UVB and UVA absorber and (b) as a quencher for reactive oxygen species. If the extract is used in its crude form without dilution, it acts partially as a UV screen. When PE is used in dilute or colorless form, it shows little or no absorption in the UVB and UVA spectrum but still shows significant free radical quenching or scavenging properties against $O_2^{\cdot-}$.

Therefore, PE acts not only as a photoprotectant but as an antioxidant. In its role as an antioxidant, PE may be used similarly to other known antioxidants (e.g., Vitamin C, Vitamin E, β-carotene) to protect the skin or other tissues against the oxidative stresses that cause cell membrane damage, DNA damage, inflammatory reactions of skin photosensitization and photoaging.

IV. Preparations for Topical Administration

In one set of embodiments, in addition to PE, the photoprotective preparations of the present invention include a pharmaceutically acceptable carrier for topical application.

Such pharmaceutically acceptable carriers are well known in the art and, in essence, may include any currently used and commercially available topical sunscreen or cosmetic preparation, or combinations of currently used and commercially available sunscreen or cosmetic preparations. Thus, one may simply modify an available sunscreen or cosmetic preparation by adding PE and adjusting, as necessary, the ratios of aqueous and non-aqueous components to maintain a consistency suitable for a topical application.

For examples of the compounds, and classes of compounds, typically found in the pharmaceutically acceptable carriers used in photoprotective preparations for topical application, see U.S. Pat. No. 5,256,404 to Martino et al. (Oct. 26, 1993) and U.S. Pat. No. 5,306,486 to McCook et al. (Apr. 26, 1994), the disclosures of which are incorporated herein by reference.

As used herein, the term "pharmaceutically acceptable carrier for topical application" means a composition suitable for topical application to human skin by spreading or rubbing, which does not cause irritation to human skin, and which can be mixed with PE to form a solution, emulsion, gel, lotion, ointment, balm, cream, or spreadable solid or paste. Such pharmaceutically acceptable carriers may include emollients, surfactants, humectants, lubricants, thickeners, waterproofing agents, bactericidal agents, percutaneous penetrating agents and preservatives. In addition, various cosmetic agents, such as fragrances and pigments may be included in a pharmaceutically acceptable carrier for topical application. As there is some evidence that orally administered PE is most effective under acidic conditions, it may be preferable that the carrier be slightly acidic or at least non-alkaline even for topical administration. Preferably, the preparation has a pH>5 but<8.

A pharmaceutically acceptable carrier for topical application may also include photoprotective agents which supplement or complement the photoprotective properties of PE. In particular, the carrier may include chemical sunscreen agents, physical sunscreen agents and/or cosmetic agents approved for use with humans (by, for example, the U.S. Food and Drug Administration and the Cosmetics, Toiletries and Fragrance Association).

As used herein, the term "physical sunscreen agent" means a compound which, when used as a component of a pharmaceutically acceptable carrier for topical application, acts to reflect and/or diffract and/or scatter ultraviolet radiation and which, when applied at a concentration of 2 μl/cm$^2$ or 2 mg/cm$^2$, provides an SPF of at least 2 when the MED is measured at 24 hrs after exposure with skin Type I to Type IV. Typical physical sunscreen agents are titanium dioxide, silicone-treated titanium dioxide, zinc oxide, ferrous oxide, ferric chloride, talc, chromium oxide, cobalt oxides, kaolin, ichthyol, and starch. Physical sunscreen agents are generally in the form of particles with diameters of 30–100 nm and preferably 30–50 nm. Many other physical sunscreen agents are known in the art and need not be recited here. As used herein, the term "physical sunscreen agent" specifically does not embrace PE.

As used herein, the term "chemical sunscreen agent" means a compound which, when used as a component of a pharmaceutically acceptable carrier for topical application, acts to absorb some radiation in the ultraviolet spectrum and which, when applied at a concentration of 2 μl/cm$^2$ or 2 mg/cm$^2$, provides an SPF of at least 2 when the MED is measured at 24 hrs after exposure with skin Type I to Type IV. Typical chemical sunscreen agents include para-amino benzoic acid (PABA) and its ester derivatives, salicylates, cinnamates, benzophenones, dihydroxyacetone, parsol 1789, melanin and various hydrocarbons. Many other chemical sunscreen agents are known in the art and need not be recited here. As used herein, the term "chemical sunscreen agent" specifically does not embrace PE.

As used herein, the term "cosmetic agent" means a pigment or fragance which may be topically applied to human skin for aesthetic effect and which does not cause irritation. Cosmetic agents are well known in the art and are included in such products as lipsticks, eye shadows, rouges, foundations and other forms of "make-up." As used herein, "cosmetic agents" are limited to those used for imparting color or fragrance to human skin. The term "cosmetic agents" is not intended to embrace other types of agents such as those used specifically in nail or hair care products. As used herein, the term "cosmetic agents" specifically does not embrace PE.

In general, the photoprotective preparations for topical application of the present invention should include at least about 1% PE by volume although, as will be understood by one of ordinary skill in the art, lesser amounts may be used with lesser advantage. In experiments with hairless mice, for example, photoprotective effects were observed for concentrations of PE as low as 0.5% in DMSO. In preferred embodiments, however, the preparation should comprise at least about 5% or 10% PE by volume. Higher concentrations, including PE at concentrations of 25%, 50% or greater, are also contemplated and intended to fall within the scope and spirit of the appended claims. As will be understood by one of ordinary skill in the art, the percentage of PE by volume will be determined in commercial applications by a variety of factors including: the desire to protect against UVA and UVB, the desire to inhibit tanning, the desire to inhibit phototoxic reaction, relative costs of different agents, the desire to include multiple agents with different photoprotective properties (e.g. chemical sunscreen agents and physical sunscreen agents), and the desire to include compounds which produce an aesthetically pleasing product which is easy to use (e.g. cosmetic pigments, emollients, perfumes, aloe, sunless "tanning" agents such as dihydroxy acetone, etc.).

As exemplary embodiments, photoprotective preparations for topical application might include, but are not limited to, those described in Example 8.

V. Preparations for systemic Administration

In order to facilitate oral adminstration, PE may be mixed with any of a variety of pharmaceutically acceptable carriers for oral administration. By the term "pharmaceutically acceptable carrier for oral administration" is meant a composition which is non-toxic, is not irritating to the human gastrointestinal system, and which can be mixed with PE to form a solution, syrup, emulsion, gel, or solid. Preparations for intravenous, intramuscular, subcutaneous or, in general, parenteral administration may also be produced by methods known in the art.

Some examples of substances which can serve as pharmaceutically acceptable carriers for oral administration are sugars such as lactose, glucose and sucrose; starches such as corn starch and potato starch; cellulose and its derivatives, such as sodium carboxymethylcellulose, ethylcellulose, and cellulose acetate; powdered tragacanth; malt; gelatin; talc; stearic acid; magnesium stearate; calcium sulfate; vegetable oils such as peanut oil, cottonseed oil, sesame oil, olive oil, and corn oil; polyols such as propylene glycol, glycerine, sorbitol, mannitol, and polyethylene glycol; polyvinylpyrrolidone; alginic acid; pyrogen-free water; isotonic saline; phosphate buffer solutions; cocoa butter; emulsifiers; as well as other non-toxic compatible substances used in pharmaceutical formulations. Wetting agents and lubricants such as magnesium stearate, as well as coloring agents, flavoring agents, excipients, tableting agents, stabilizers, antioxidants, and preservatives, can also be present. Other compatible pharmaceutical additives and actives may be included in the pharmaceutically acceptable carrier for use in the compositions of the present invention.

The preparations for oral administration may be in the form of tablets, caplets, soft and hard gelatin capsules, pills, including delayed or prolonged release formulations, dispersible powders or granules, lozenges, sachets, cachets, elixirs, suspensions, emulsions, solutions, syrups, aerosols, (as a solid or in a liquid medium), and the like.

In one preferred embodiment, the PE is formed into a capsule with lactose and magnesium stearate (a lubricant) as a pharmaceutically acceptable carrier for oral administration. As some individuals are lactose-intolerant, however, an alternative carrier, such as a starch or vegetable oil, may be preferred.

As exemplary embodiments, photoprotective preparations for oral administration might include, but are not limited to, those described in Example 9.

VI. Methods of Providing Photoprotection

1. Topical Photoprotection with PE

In one embodiment of the present invention, a method of providing photoprotection (including protection or prevention of photoaging, actinic damage and skin cancers) is disclosed which employs a preparation of PE for topical application.

In a preferred embodiment, a PE preparation is formulated as a solution, emulsion, gel, ointment, lotion, balm, cream, or spreadable solid or paste which may be applied to the skin of an individual and smeared over the skin to form a thin layer. The preparation should be applied before exposure to ultraviolet radiation and should be reapplied after swimming, bathing, or significant perspiration.

Preferably, the PE preparation also includes other sunscreen agents (physical or chemical), emollients, surfactants, humectants, lubricants, thickeners, waterproofing agents, and/or preservatives. The overall SPF provided by the preparation should be at least 2. Different formulations may be employed for individuals with different skin types and expected exposure times and, therefore, formulations with SPFs equal to or greater than 5, 10, 15, 20 and 30 are contemplated. For individuals with highly photosensitive skin, formulations with an SPF of equal to or greater than 40 or 50 may also be employed.

2. Oral Photoprotection with PE

In another embodiment of the present invention, a method of providing photoprotection (including protection or prevention of photoaging, actinic damage and skin cancers) is disclosed which employs a preparation of PE for oral administration.

In a preferred embodiment, the PE is formulated as a capsule in which lactose and magnesium stearate serve as the pharmaceutically acceptable carrier. As some individuals are lactose-intolerant, however, an alternative carrier, such as a starch or vegetable oil, may be preferred. The capsules contain, preferably, about 100–150 mg of PE and, most preferably, 120 mg of PE.

Because PE appears to be absorbed better under acid conditions, the capsules are preferably not taken with an antacid and, most preferably, are taken at least one half hour before a meal. Similarly, because alcohol appears to reduce the absorption and efficacy of PE, the preparation is preferably not administered with alcoholic beverages.

As PE appears to enhance the effect of the drug digitalis, individuals Taking digitalis should consult a physician before using an orally administered PE preparation and, if appropriate, the dosage of digitalis should be reduced. Preferably, PE is not used by individuals taking digitalis.

For adults, the dosage of PE should be at least 120 mg taken within 3 hrs prior to solar or other ultraviolet radiation exposure. More preferably, the dosage is between 360 and 720 mg taken within 3 hrs before exposure. PE has been shown to be safe at dosages up to 1200 mg/day and, therefore, dosages of up to 1200 mg may be taken in the 24 hrs prior to exposure. Preferably, the dosage of PE should be at least 360 mg taken within 24 hrs prior to exposure. More preferably, the dosage is between 720 and 1440 mg taken within 24 hrs before exposure. In addition, daily dosages of 360–720 mg/day may be taken in the days preceding exposure although the effect appears not to be substantially cumulative after the second day.

For children over 6 years of age, dosages should be limited to 120–240 mg per day.

In the event that digestive discomfort results from an oral PE preparation, use of the preparation should be discontinued. For lactose-intolerant individuals, ingestion of small amounts (e.g. 120–180 mg) of lactose is probably not sufficient to cause symptoms of intolerance but, in case diarrhea develops, use of the product should be discontinued. Alternatively, PE preparations lacking lactose (substituting, for example, a starch or vegetable oil as the carrier) may be employed.

III. Examples

1. Preparation of PE

Developed *Polypodium leucotomos* rhizomes may be separated from African Palm trees, with which they grow symbiotically, and transplanted to plantations where soil and weather conditions are favorable (e.g. Yojoa Lake, Honduras). After complete development and sporulation of the leaves, the aerial parts of the plant may be harvested and dried for 24 hrs. at temperatures between 60°–70° C. A batch of 160 kg of the dried leaves may be finely ground and subjected three times to 10 hrs of low reflux extraction in of methanol/water (total volume 1430 liters). The resulting dilute extract may then be concentrated using negative pressure evaporation at 25°–50° C. to remove most of the alcohol and to reduce the volume to approximately 20% of the original. Optionally but preferably, lipids may be removed from the concentrated extract with a hydrophobic solvent such as n-hexane and cations may be removed with an ionic interchange resin. Optionally but preferably, tannins, chlorophyll and other pigments may be partially removed using activated charcoal (200–300 g per kg of original dried leaves). Finally, the extract may be filtered and concentrated under negative pressure to yield approximately 16 kg of concentrated PE. The resulting PE should have an amber to brown color and a syrupy consistency.

The PE used in the experiments described below was derived from *Polypodium leucotomos* and provided by Industrial Farmacéutica Cantabria, S.A., Madrid, Spain.

2. Topical Application of PE to Normal Individuals

Five subjects were selected randomly from a group of 30 healthy male and female volunteers. They were fair skinned volunteers of Type III or Type IV skin, aged 18 to 35, who had no systemic or cutaneous diseases, had no history of drug photosensitivity, showed no abnormal reactivity to sunlight, and received no other medications. All subjects were able to show good tanning response after exposure to sunlight.

The volunteers were prepared for sun exposure as follows:

Adhesive templates with multiple exposure windows were affixed to the backs of the subjects. Each window was 2×2 cm in size. Templates were affixed on both the left and right sides of the spinal column in the infrascapular region.

One row of six exposure windows on each subject was used to determine the MED of the subject's untreated (unprotected) skin. The windows of this row were exposed to solar radiation for 12.5', 15', 20', 25', 30', and either 35' or 40'.

All other rows were exposed for 20', 40', 60', 80', 100' or longer. Of these rows, one was used as a negative control (with no topical application). Another row was used as a positive control with topical applications of a commercially available sunscreen with an SPF of 15 ("Std SPF 15": contains 3% Parsol 1789 and 3–5% benzophenone-3). The remaining four rows were used for the 10%, 25%, 50% 1×, and 50% 2× PE applications. Applications of test products were made 30 minutes before sun exposure. The applied products were allowed to dry at ambient temperature.

Subjects were assembled in a open field. They were asked to lie down in a prone position on air mattresses assigned individually to each subject. Sunlight exposures were given between 11:30 a.m. and 1:30 p.m. The sunlight intensity was measured with a precalibrated radiometer (International Light Co., Newburyport, Mass.) and averaged 27 w/m$^2$. This level of flux, when given to untreated skin for 30 minutes, is equivalent to about 50 mJ/cm$^2$ of solar radiation, a dose adequate to produce a minimally perceptible sunburn reaction in individuals of skin Type III or IV. Sun exposure times were as follows:

| MED Row | Control Row | 10% PE Row | 25% PE Row | 50% 1× PE Row | 50% 2× PE Row |
|---|---|---|---|---|---|
| 12.5' | 20' | 20' | 20' | 20' | 20' |
| 15.0' | 40' | 40' | 40' | 40' | 40' |
| 20' | 60' | 60' | 60' | 60' | 60' |
| 25' | 80' | 80' | 80' | 80' | 80' |
| 30' | 100' | 100' | 100' | 100' | 100' |
| 35'/40' | 100' | 100' | 100' | 100' | 100' |

After delivering the appropriate sun exposure doses, test sites were covered with UV-opaque adhesive tape. Observations of all exposed sites were made: (1) immediately after exposure for IPD determination; (2) at 24 hours after exposure for MED determination and SPF assessment; and (3) on the sixth day after exposure for MMD determination.

| Treatment | Minimum Dose for IPD (in min.) | Minimum Dose for IPD (in mJ/cm$^2$)* | Protection Factor |
|---|---|---|---|
| (1) Control | 25.9 | 43.1 | — |
| (2) 10% PE | 56.9 | 94.8 | 2.16 |
| (3) 25% PE | 68.0 | 113.3 | 2.63 |
| (4) 50% 1× PE | 88.0 | 147.0 | 3.40 |
| (5) 50% 2× PE | 92.0 | 153.0 | 3.55 |
| (6) Std SPF 15 | 80.0 | 133.6 | 3.09 |

*Flux of UVB component. One minute of exposure ≈ 1.66 mJ/cm$^2$.

The increment in the UV dose required for the immediate pigment darkening (IPD) reaction is clearly related to the concentration of PE applied topically. Topically applied PE protected by retarding or prolonging the photo-oxidation reaction of melanin pigment already present in the skin.

To determine the effects of the PE applications on MED, the sun-exposed subjects were evaluated for erythema at 24 hours. PE-treated skin sites received a maximum sun exposure of 100 minutes, a dose equivalent to approximately 3 MED. This dose of 3 MED can produce mild to moderate sunburn reaction (pink-red color without painful burn). The table below presents the MED values as well as the calculated sunscreen protection factors (SPF) for the different applications of the test formulations:

| Treatment | Minimum Erythematic Dose (MED) (in min.) | Minimum Erythematic Dose (MED) (in mJ/cm$^2$)* | SPF |
|---|---|---|---|
| (1) Control | 34.0 | 56.0 | — |
| (2) 10% PE | 80.0 | 133.0 | 2.35 |
| (3) 25% PE | 92.0 | 153.0 | 2.71 |
| (4) 50% 1× PE | >100.0 | >168.0 | >2.94 |
| (5) 50% 2× PE | >100.0 | >168.0 | >2.94 |
| (6) Std SPF 15 | >100.0 | >168.0 | >2.94 |

*Flux of UVB component. One minute of exposure ≈ 1.66 mJ/cm$^2$.

Each of the four PE containing test products showed effective protection and none of the PE-protected sites showed visible sunburn reaction. Because the total exposure time was limited to approximately 100' to avoid the risk of substantial sunburn to any subject, the exposure was insufficient to cause erythema with the 50% 1×, 50% 2× and Std SPF 15 sunscreens. Thus, the actual MEDs of these applications and SPF values of these formulations remain to be established (although they are clearly greater than 2.94).

The third criterion to demonstrate the photoprotective effect of topical PE was to determine the minimal melanogenic dose (MMD) of UV radiation required to stimulate delayed pigmentation or neomelanogenesis (tanning reaction) in untreated control skin and the UV dose required to stimulate delayed pigmentation of the PE treated skin. The delayed pigmentation response appears to be due to the cumulative effects of longwave ultraviolet radiation (>320 nm).

The table below reports the minimal melanogenic dose (MMD) required to stimulate delayed pigmentation (tanning) reaction at control (unprotected or untreated) sites and at sites protected by 10%, 25%, 50% 1× and 50% 2× PE. The observed minimal melanogenic dose values shown below are consistent with the photoprotective nature of PE.

| Treatment | Minimal Melanogenic Dose (MMD) | |
| --- | --- | --- |
| | (in min.) | (in mJ/cm$^2$)* |
| Control | 44.0 | 75.0 |
| 10% PE | >88.0 | >147.0 |
| 25% PE | >92.0 | >153.0 |
| 50% 1× PE | >100.0 | >167.0 |
| 50% 2× PE | >100.0 | >167.0 |
| Std SPF 15 | >100.0 | >167.0 |

*Flux of UVB component. One minute of exposure ≈ 1.66 mJ/cm$^2$.

Again, each of the PE preparations afforded significant protection and, because the total exposure time was limited to approximately 100' to avoid burning any subjects, the exposure was insufficient to cause neomelanogenesis with the 50% 1×, 50% 2× and Std SPF 15 sunscreens. Thus, the actual MMDs of these applications remain to be established (although they are clearly greater than 167 mJ/cm$^2$).

3. Oral Administration of PE to Normal Individuals

After establishing the safety and non-toxicity of oral PE at dosages greater than 1000 mg per day, we decided to administer PE orally, twice daily to human volunteers of skin Type III and IV. The subjects were divided into two test groups. In the first group of subjects, the "two day" group, three normal subjects received 720 mg PE the day prior to sun exposure and an additional dose of 720 mg PE three hours before sun exposure (total dose 1440 mg). In the second group, the "5 day" group, five normal subjects received 720 mg of PE each day for four consecutive days before sun exposure and 720 mg of PE three hours before exposure on the fifth day. Two additional groups of eight subjects each, a control group receiving no PE, and a group using the Std SPF 15 sunscreen, also were tested.

All of the subjects were exposed under identical conditions to solar ultraviolet radiation from 11:00 a.m. to 2:00 p.m. Adhesive templates with pre-cut rows of five exposure windows, each 2 cm×2 cm in size were affixed to the backs (infrascapular regions) of the volunteers. Each volunteer had a minimum of five exposure rows symmetrically placed on the left and right side of the spinal column. Each row had five or six exposure windows 2×2 cm in size. Sun-exposed sites were covered with a UV-opaque adhesive tape at the end of each measured exposure dose.

The responses to the graded doses of sun exposure, ranging from 30 minutes (about 1MED) to 45, 60, 90, 120, 150, or 180 minutes, were evaluated in terms of: (1) Minimal dose of solar radiation required for immediate pigment darkening (IPD) response measured at the end of the exposure period; (2) Minimal erythematic dose (FLED) of solar radiation required for minimal erythema reaction measured 24 hours after the exposure period; and (3) Minimal melanogenic dose required (MMD) for delayed pigment response measured 3 days (72 hrs) after the exposure period.

The results for immediate pigment darkening (IPD) response of control subjects (no PE), PE-treated subjects, and sunscreen-protected subjects were as follows:

| Treatment | number of subjects | Minimum Dose for IPD | | Protection Factor |
| --- | --- | --- | --- | --- |
| | | (in min.) | (in mJ/cm$^2$)* | |
| (1) Control | 8 | 25.9 | 43.2 | — |
| (2) PE 2 days | 3 | 70.0 | 116.7 | 2.70 |
| (3) PE 5 days | 5 | >80.0 | >133.3 | >3.09 |
| (4) Std SPF 15 | 8 | >80.0 | >133.3 | >3.09 |

*Flux of UVB component. One minute of exposure ≈ 1.66 mJ/cm$^2$.

It is clear from the tabulated data that orally administered PE was photoprotective. A slightly better protection was observed after 5 days of oral PE ingestion (total dose 3600 mg) than that observed after two oral doses of PE (total dose 1440 mg). This difference in SPF values was not significant. Therefore, there may not be a substantial accumulation of the photoprotective effect beyond two days of oral doses at 720 mg/day. It is possible that the photoprotective component of PE is not retained in the blood or skin for an extended period but, rather, is metabolized and rapidly excreted in the urine.

To evaluate the effect of oral PE on MED, it was possible to use the same subjects as their own controls. Thus, the minimal erythema dose (MED) for each of the eight test subjects (three from the 2 day group and five from the 5 day group) was determined prior to administration of PE to obtain the MED values of sunburn response of untreated control skin. Then, the MEDs of the same eight test volunteers were determined after they had consumed PE orally for two or five days.

The results are presented below:

| Treatment | Minimum Erythematic Dose (MED) | | SPF |
| --- | --- | --- | --- |
| | (in min.) | (in mJ/cm$^2$)* | |
| (1) Control | 34.0 | 56.6 | — |
| (2) PE 2 days | 90.0 | 150.0 | 2.65 |
| (3) PE 5 days | 100.0 | 166.7 | 2.94 |

*Flux of UVB component. One minute of exposure ≈ 1.66 mJ/cm$^2$.

The data indicate the orally administered PE enhances the MED values nearly three fold. The orally administered PE (3600 mg) given for five consecutive days produced a photoprotection factor of 2.94 whereas the orally administered PE given for 2 days (1440 mg) produced a photoprotection factor of 2.65. This suggests that PE is photoprotective even after only two days of oral dosages. The data also reveal that there was no significant additional enhancement of photoprotection when the PE dosages were repeated daily for 5 days. Thus, the data appear to demonstrate a maximum photoprotective effect of PE within 3 to 24 hours after the oral ingestion of the PE and that the photoprotective effect of PE is not cumulative after this period.

It is of further interest to note that the skin of the PE-treated subjects showed no evidence of sunburn reaction when the subjects were exposed to graded dosages of solar radiation ranging as high as 150 or 180 minutes. In contrast, the response of control skin receiving no oral PE showed evidence of sunburn reaction after exposure to only 30 to 34 minutes of midday solar radiation. Sun exposure of unprotected control skin for sixty minutes produced a moderate degree of sunburn reaction with tenderness.

In order to assess the effects of orally administered PE on delayed tanning response or neomelanogenesis, healthy subjects were selected randomly. For these subjects (a) the minimum melanogenic dose (MMD) required for the induction of delayed tanning reaction was evaluated without the administration of PE and (b) the MMD of the same volunteers was determined after they had received oral doses of PE (720 mg/day) either for two consecutive days or for five consecutive days. As a positive control we also measured the dose required for the induction of delayed tanning response in skin well protected by the Std SPF 15 sunscreen. Due to time constraints, the induction of delayed pigment response was evaluated 72 hours rather than on day 5 (120 hrs) after sun exposure. The results are tabulated below:

| Treatment | number of subjects | Min. Melanogenic Dose (in min.) | (in mJ/cm$^2$)* | Pigment Response |
|---|---|---|---|---|
| (1) Control | 5 | 45.0 | 75 | moderate |
| (2) PE 2 days | 3 | 75.0' | 125 | minimal |
| (3) PE 5 days | 5 | 90.0' | 150 | weak |
| (4) Std SPF 15 | 5 | >150.0 | >250 | minimal |

*Flux of UVB component. One minute of exposure ≈ 1.66 mJ/cm$^2$.

The data show that oral PE is photoprotective and the dose required for induction of delayed tanning response in PE protected skin is much greater than the dose required for the induction of delayed tanning response in unprotected skin.

Thus by determining the dose required for the induction of delayed tanning response of skin protected by orally administered PE, we have shown that PE is indeed photoprotective against sunburn reaction and the induction of melanin pigmentation (delayed tanning reaction).

4. Topical Application of PE on Photosensitized Individuals

As another means of assessing the photoprotective properties of PE, topical applications of PE were tested on subjects deliberately made photosensitive by oral administration of psoralens. The psoralens 8-methoxypsoralen (8-MOP) and 5-methoxypsoralen (5-MOP) are widely used in the United States and throughout the world in the treatment of psoriasis and vitiligo in conjunction with exposure to UVA radiation (320–400 nm) from artificial light sources or from solar radiation. These drugs are known to increase the photosensitivity of the skin by participating in a phototoxic reaction with ultraviolet radiation and, thereby, to induce erythema, edema and tenderness of the skin.

PUVA (P=psoralen; UVA=ultraviolet A) is a standard protocol which involves the oral ingestion of psoralens and subsequent exposure of the skin to ultraviolet radiation. Normal Type III or Type IV skin exposed to solar radiation (320–400 nm) for up to 45 minutes without the drug 8-MOP or 5-MOP shows no redness or phototoxic reaction (i.e. "sunburn") when examined 48 to 72 hours after exposure. In skin photosensitized with oral 8-MOP or oral 5-MOP, however, skin exposed to solar radiation for as little as 10 minutes may show a gradually increasing degree of phototoxicity or sunburn when examined 48 to 72 hours after the exposure. The dose of ultraviolet radiation necessary to produce skin photosensitization and phototoxicity is defined as the minimum phototoxic dose (MPD). Thus, the psoralens 8-MOP and 5-MOP photosensitize the skin and cause a measurable degree of phototoxic reaction. Specifically, with orally administered 5-MOP or 8-MOP, a much lower (three- to five-fold) dose of UVA radiation is necessary to produce redness and phototoxicity. Using PUVA as an assay, one can establish the photoprotective properties of a preparation by measuring its ability to inhibit phototoxicity in 8-MOP or 5-MOP photosensitized skin.

As above, we selected four normal human subjects of skin Type III or IV to demonstrate the ability of PE to retard the phototoxic reaction of 8-MOP or 5-MOP. 8-MOP was administered to two subjects at a dose of 0.45–0.6 mg per kg, about 1.5–2 hrs before exposure to solar UVA radiation. 5-MOP, a weaker phototoxic drug than 8-MOP, was administered to two different subjects at the higher dose of 1.0–1.2 mg per kg, 1.5–2 hrs before exposure. For each group of subjects, the minimum phototoxic dose (MPD) was then determined by examining them for redness and photodamage 72 hours after sun exposure.

We then assessed the photoprotective properties of PE by determining the minimal phototoxic dose (MPD) of UV required for subjects receiving topical application of PE after oral administration of either 8-MOP (0.6 mg/kg) or 5-MOP (1.0–1.2 mg/kg) 1.5–2 hrs before exposure to midday sun.

Each subject received topical applications (2 μl/cm$^2$) of formulations containing 10%, 25%, and 50% PE in lotion form at preassigned sites demarked by adhesive templates with 2×2 cm exposure windows. One of the templates sites was used for the application of the Std SPF 15 sunscreen to serve as an internal standard. One additional template site did not receive any topical application and this site served as a non-treated control site for assessing the MPD value of skin without any photoprotection.

The results for orally administered 8-MOP and topically applied PE are presented below:

| | MPD Measured at 72 hrs | | Protection |
|---|---|---|---|
| | (in min.) | (in J/cm$^2$)* | Factor |
| (1) Oral 8-MOP (untreated skin) | 7.5 | 2.0 | — |
| (2) Oral 8-MOP + topical 10% PE | >30.0 | >8.0 | >4.0 |
| (3) Oral 8-MOP + topical 25% PE | >30.0 | >8.0 | >4.0 |
| (4) Oral 8-MOP + topical 50% PE | >30.0 | >8.0 | >4.0 |
| (5) Oral 8-MOP + Std SPF 15 | >30.0 | >8.0 | >4.0 |

*Flux of UVA component. One minute exposure ≈ 0.267 J/cm$^2$.

The results for orally administered 5-MOP and topically applied PE are presented below:

|  | MPD Measured at 72 hrs | | Protection |
| --- | --- | --- | --- |
|  | (in min.) | (in J/cm$^2$)* | Factor |
| (1) Oral 5-MOP (untreated skin) | 20.0 | 5.3 | — |
| (2) Oral 5-MOP + topical 10% PE | >30.0 | >8.0 | >1.5 |
| (3) Oral 5-MOP + topical 25% PE | >45.0 | >12.0 | >2.2 |
| (4) Oral 5-MOP + topical 50% PE | >45.0 | >12.0 | >2.2 |
| (5) Oral 5-MOP + Std SPF 15 | >57.5 | >17.0 | >3.0 |

*Flux of UVA component. One minute exposure ≈ 0.267 J/cm$^2$.

These data show that topically administered PE is photoprotective of skin photosensitized by either 8-MOP or 5-MOP. It should be recalled that orally administered 5-MOP is less phototoxic than orally administered 8-MOP. This explains the requirement of higher doses for MPD determination with 5-MOP than that required for MPD determination of 8-MOP. As in the previous experiments, in order to avoid the risk of causing significant sunburns including blistering reaction to the human subjects, exposure times were purposely limited. As a result, the actual MPDs and protection factors remain to be established (although PE clearly provided a protection factor of at least 1.5 to at least 4.0).

5. Oral Administration of PE to Photosensitized Individuals

The photoprotective effects of orally administered PE were also evaluated in subjects receiving the skin photosensitizing drugs 8-MOP and 5-MOP as follows: Four subjects of skin Type III or IV were selected. Two of these four subjects were given oral dosages of the drug 8-MOP (0.6 mg/kg) two hours prior to sun exposure. The other two subjects were given oral 5-MOP (1.0–1.2 mg/kg) 2 hours before sun exposure. The minimal phototoxic doses (MPD) of the unprotected skin of these test subjects were then evaluated at 72 hours to obtain the control MPD values without PE.

Each of these same subjects were then retested on previously unexposed skin with PE as a photoprotectant. They were given oral dosages of 1440 mg PE (720mg PE 18 hours before sun exposure and 720 mg PE three hours before sun exposure). Then, as before, they were given an oral dose of either 8-MOP (0.6 mg/kg) or 5-MOP (1.0–1.2 mg/kg) two hours before sun exposure. The subjects were examined 72 hours after exposure to determine the MPD in the presence of orally administered PE and psoralen.

The results of the tests with orally administered 8-MOP and orally administered PE are presented below:

|  | MPD Measured at 72 hrs | | Protection |
| --- | --- | --- | --- |
|  | (in min.) | (in J/cm$^2$)* | Factor |
| (1) Oral 8-MOP only (control) | 7.5 | 2.0 | — |
| (2) Oral 8-MOP + 1440 mg oral PE | 52.5 | 14.0 | 7.0 |

*Flux of UVA component. One minute exposure ≈ 0.267 J/cm$^2$.

The results of the tests with orally administered 5-MOP and orally administered PE are presented below:

|  | MPD Measured at 72 hrs | | Protection |
| --- | --- | --- | --- |
|  | (in min.) | (in J/cm$^2$)* | Factor |
| (1) Oral 5-MOP only (control) | 15.0 | 4.0 | — |
| (2) Oral 5-MOP + 1440 mg oral PE | 45.0 | 12.0 | 3.0 |

*Flux of UVA component. One minute exposure ≈ 0.267 J/cm$^2$.

These results establish the phototoxicity photoprotection property of orally administered PE. This natural extract enhanced the MPD values for skin photosensitization induced by either of the psoralens 5-MOP or 8-MOP by a factor of three to seven-fold, respectively.

6. Superoxide Anion Quenching by PE

The formation of $O_2^{\cdot-}$ radicals (superoxide anions) was carried out by using riboflavin (RF), a well known generator for superoxide anions (see Carraro and Pathak, *J. Invest. Dermatol.* 90:267–275, 1988; Beauchamp and Fridovich, *Anal. Biochem.* 44:276–287, 1971). The production of $O_2^{\cdot-}$ was ascertained spectrophotometrically by monitoring the riboflavin photosensitized reduction of nitro blue tetrazolium (NBT) to nitro blue diformazan (NBF) at 560 nm by the reaction $NBT + 4O_2^{\cdot-} \rightarrow NBF + 4O_2$. The generation of $O_2^{\cdot-}$ was quantitatively estimated as a function of increasing exposure dose of UVA (1–10 J/cm$^2$) and by recording the increase in optical density value at 560 nm for the irradiated solution. Quenching of $O_2^{\cdot-}$ production was confirmed by using superoxide dismutase (50 units/mL) and an aliquot of a diluted colorless solution of PE (0.01% or less). The scavenging potential of PE was also evaluated by increasing the irradiation dose of UVA (0.5–10 J/cm$^2$) and observing the percentage quenching of the generated $O_2^{\cdot-}$ by adding an aliquot of PE into the reaction system.

Figure 2:
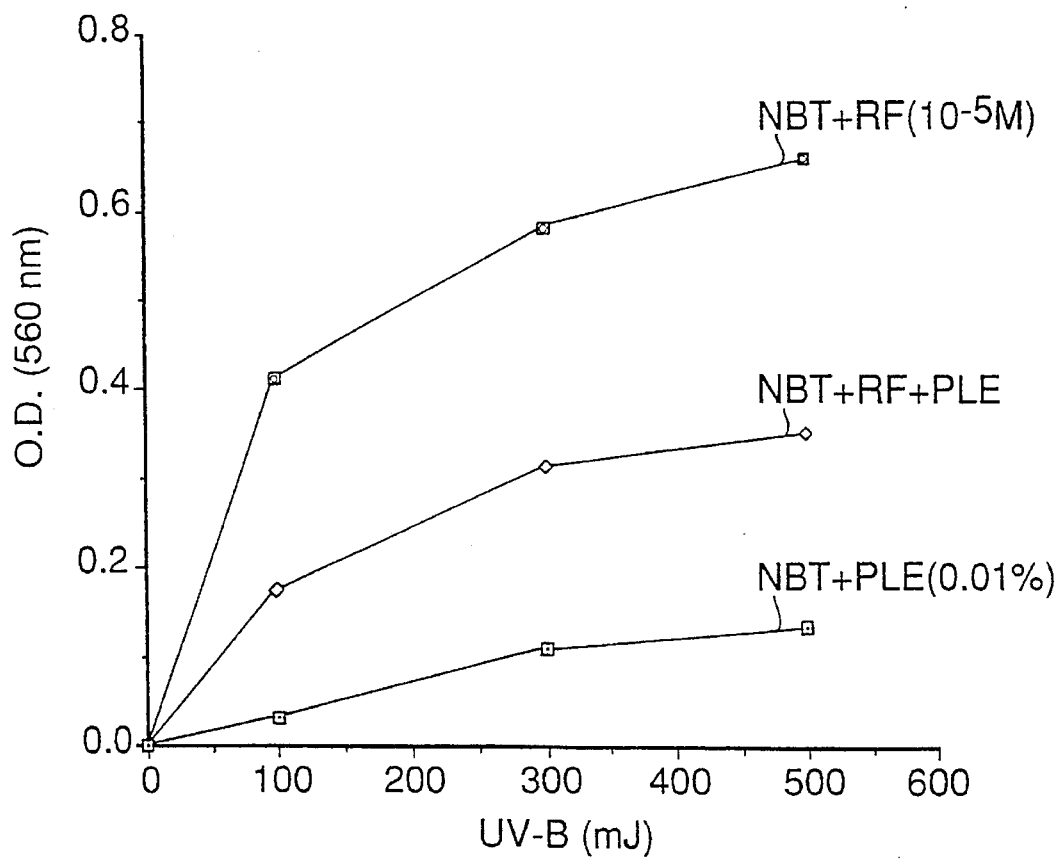
FIG. 2 plots the generation of superoxide anion as a function of UVB dose. Superoxide anion generation is measured by changes in optical density at 560 nm resulting from the conversion of NBT to NBF by reaction with superoxide anion. Riboflavin (RF) was used as a photosensitizer. From top to bottom, the three graphs show the superoxide anion generation by RF alone, by RF in the presence of Polypodium extract (PE), and by PE alone.

The results pertaining to this investigation are shown in FIG. 1 and FIG. 2. The radiation source used was polychromatic and produced a major fraction of UVB as well as some fraction of UVA radiatioN. The UV radiation produced $O_2^{\cdot-}$ and the increase in the generation of $O_2^{\cdot-}$ with increased irradiation dose is clear. PE alone contributed little to the production of $O_2^{\cdot-}$. In the presence of riboflavin, however, there was significant generation of $O_2^{\cdot-}$. When $O_2^{\cdot-}$ generation was studied in the presence of both riboflavin and PE (0.01%), a substantial reduction in the yield of $O_2^{\cdot-}$ was observed. When riboflavin and UVA or riboflavin and UVB systems were used for the generation of $O_2^{\cdot-}$, the addition of PE produced 42.2% and 55% reductions in $O_2^{\cdot-}$ production respectively. We could not produce 100% quenching in the production of $O_2^{\cdot-}$ because of the opacity and turbidity that resulted with higher concentrations of PE interfered with the spectrophotometric determination.

7. Singlet Oxygen Quenching by PE

The formation and detection of $^1O_2$ (singlet oxygen) was conducted by known methods (see Kraljic and Mohsni, *Photochem. Photobiol.* 28:577–581, 1978). A 5 mL solution of N,N-dimethyl-p-nitrosoaniline (RNO, 0.35–9.4×10$^{-5}$M) in 0.05M phosphate buffer, pH 7.0, was mixed with 10$^{-2}$M histidine (HIS used as a selective acceptor of $^1O_2$) and a known photosensitizer, such as hematoporphyrin derivative, rose bengal, methylene blue, or a psoralen (3-carbethoxypsoralen) at 10$^{-5}$M concentration. These solutions with RNO and a photosensitizer were irradiated with UVA (1–10

J/cm$^2$) and the subsequent bleaching of RNO was recorded spectrophotometrically at 440 nm. The scavenging potential of PE was compared with known $^1O_2$ scavengers (e.g., NaN$_3$ or 1,4-diazabicyclo (2.2.2) octane (DABCO)) used as reference compounds. The inhibition of $^1O_2$ production was expressed as s percentage of the control values (without NaN$_3$ or DABCO).

Figure 3:
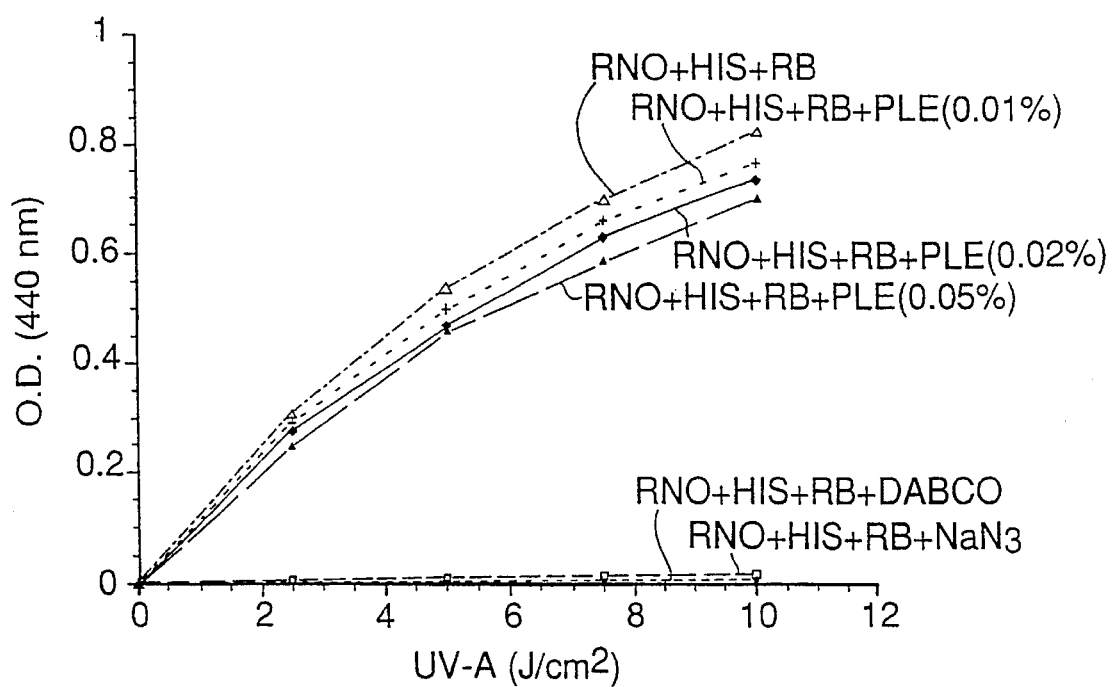
FIG. 3 plots the generation of singlet oxygen as a function of UVA dose. Singlet oxygen generation is measured by changes in optical density at 440 nm resulting from the bleaching of N,N-dimethyl-p-nitrosoaniline (RNO). Histidine (HIS) was used as a selective acceptor of singlet oxygen. Rose Bengal (RB) was used as a photosensitizer. From top to bottom, the top four graphs show the singlet oxygen generation by RB alone, by RB in the presence of 0.01% Polypodium extract (PE), by RB in the presence of 0.02% PE, and by RB in the presence of 0.05% PE. The bottom two graphs show the generation of singlet oxygen in the presence of RB and the known singlet oxygen scavengers NaN and DABCO.

The data on the production of $^1O_2$ obtained with rose bengal (RB 10$^{-5}$M) with and without the presence of PE are shown in FIG. 3. Unlike NaN$_3$ and DABCO, which are well known quenchers of $^1O_2$ and which produced almost 100% inhibition in the rate of $^1O_2$ production, the effects of PE on the inhibition of $^1O_2$ production were less pronounced. Less than 10% inhibition in the production of $^1O_2$ could be observed.

8. Formulations for Topical Application

| Ingredient | % w/w | | | |
|---|---|---|---|---|
| | Lotion | Gel | Solution | Cream |
| PE | 6.00 | 6.00 | 6.00 | 15.00 |
| Hygroplex HHG | 5.00 | 5.00 | 5.00 | 5.00 |
| Vitamin E acetate | 0.20 | — | — | 0.50 |
| Cetyl alcohol | 3.00 | — | — | — |
| EDTA Na$^{2+}$ | 0.10 | 0.10 | — | — |
| Glycerin | 5.10 | 9.25 | 6.00 | 6.00 |
| Hydroxyethyl cellulose | 1.02 | 1.85 | — | — |
| Perfume | 0.12 | 0.12 | 0.20 | 0.30 |
| Distilled water | s/q | s/q | s/q | s/q |
| Kathon CG (bactericide) | 0.20 | 0.20 | 0.20 | 0.20 |
| Butyl hydroxytoluene | — | 0.01 | 0.01 | — |
| Polysorbate (Tween 80) | — | — | 0.20 | — |
| Alcohol 96 | — | — | 10.00 | 2.00 |
| Ixafin 15 | — | — | — | 15.00 |
| Methylparaben | — | — | — | 0.20 |
| Propylparaben | — | — | — | 0.10 |
| Tensioderm | — | — | — | 1.00 |
| Isopropyl myristate | — | — | — | 1.50 |

9. Formulations for Oral Administration 18 kg of corn starch is added to 12.6 kg of concentrated PE syrup and mixed until a homogeneous mass is obtained. The mass is dessicated in a heat cabinet at 35°–40° C. for 8 hrs. Then dried mass is then filtered through a mesh N 40 DIN. After 45' of mixing, 18 kg of lactose and 1.5 kg of magnesium stearate are added. Hard gelatin capsules (size 0) are filled with the resulting powder. The average capsule weighs 495 mg and contains

| PE | 126 mg* |
|---|---|
| Corn starch | 180 mg |
| Lactose | 180 mg |
| Magnesium stearate | 15 mg |

*A 5% excess is used to compensate for potential loss during the manufacturing process.

As an alternative, the 18 kg of lactose may be replaced with 10 kg of microcrystalline cellulose and 8 kg polyvinylpyrrolidone.

Although the invention has been described above with respect to various presently preferred embodiments, it will be apparent to one of ordinary skill in the art that many variations and modifications may be made. Therefore, the invention is not to be understood as limited to the particular embodiments recited herein but, rather, is to be understood as embracing all such variations and modifications which fall within the spirit and scope of the claims appended hereto.

We claim:

1. A preparation for topical application comprising an effective amount of a Polypodium extract for photoprotection when applied topically to the skin and a pharmaceutically acceptable topical carrier, the preparation formulated as a topical preparation, wherein the preparation includes a composition selected from the group consisting of physical sunscreen agents, chemical sunscreen agents and cosmetic agents.

2. A preparation as in claim 1, wherein said carrier includes a chemical sunscreen agent.

3. A preparation as in claim 1, wherein said preparation includes at least about 1% Polypodium extract by weight.

4. A preparation as in claim 1, wherein said preparation includes at least about 10% Polypodium extract by weight.

5. A preparation as in claim 1, wherein said preparation includes at least about 25% Polypodium extract by weight.

6. A preparation as in claim 1, wherein said preparation includes at least about 50% Polypodium extract by weight.

7. A preparation as in claim 1 wherein said preparation provides a sun protection factor (SPF) for a minimal erythematic dose (MED) evaluated at 24 hours of at least 2 when applied at 2 µl/cm$^2$ to normal skin of Type I to Type IV.

8. A preparation as in claim 7 wherein said preparation provides a sun protection factor of at least 5.

9. A preparation as in claim 7 wherein said preparation provides a sun protection factor of at least 10.

10. A preparation as in claim 7 wherein said preparation provides a sun protection factor of at least 15.

11. A preparation as in claim 1 wherein said extract is a *Polypodium aureum* extract.

12. A preparation as in claim 1 wherein said extract is a *Polypodium crassifolium* extract.

13. A preparation as in claim 1 wherein said extract is a *Polypodium decumanum* extract.

14. A preparation as in claim 1 wherein said extract is a *Polypodium lanceolatum* extract.

15. A preparation as in claim 1 wherein said extract is a *Polypodium leucotomos* extract.

16. A preparation as in claim 1 wherein said extract is a *Polypodium percussum* extract.

17. A preparation as in claim 1 wherein said extract is a *Polypodium triseriale* extract.

18. A preparation as in claim 1 wherein said extract is a *Polypodium vulgare* extract.

19. The preparation of claim 1, wherein the carrier includes a physical sunscreen agent selected from the group consisting of titanium dioxide, silicone-treated titanium dioxide, zinc oxide, ferrous oxide, ferric chloride, talc, chromium oxide, and cobalt oxide.

20. The preparation of claim 1, wherein the carrier includes a chemical sunscreen agent and wherein the chemical sunscreen agent is selected from the group consisting of para-amino benzoic acid, esters of para-amino benzoic acid, salicylates, cinnamates, benzophenones, dihydroxyacetone, parasol 1789, and melanin.

21. A preparation as in claim 1, wherein said preparation includes between 1% and less than 3% Polypodium extract.

22. A preparation as in claim 1, wherein said preparation is prepared by an alcohol extraction of a leaf or a rhizome of a Polypodium plant.

23. A preparation for topical application comprising an effective amount for photoprotection of a Polypodium extract and a pharmaceutically acceptable carrier for topical application, wherein the Polypodium extract is selected from the group consisting of *Polypodium leucotomos, Polypodium percussum,* and *Polypodium triseriale.*

24. A method of providing photoprotection to an individual with normal skin comprising topically applying an effective amount for photoprotection of the preparation of claim 1 to said skin prior to exposure to ultraviolet radiation.

25. A method of providing photoprotection to an individual with normal skin comprising orally administering to said individual an effective amount for photoprotection of a dosage of a Polypodium extract within 2 days prior to exposure to ultraviolet radiation.

26. The method of claim 25 wherein said individual is an adult and said dosage is between 720 mg and 1440 mg taken within a 24 hour period prior to exposure to ultraviolet radiation.

27. The method of claim 25 wherein said individual is an adult and said dosage is between 360 mg and 720 mg taken within a 3 hour period prior to exposure to ultraviolet radiation.

28. A packaged product comprising a container, a preparation comprising a Polypodium extract and a pharmaceutically acceptable carrier for oral administration within said container, and instructions for oral administration of said preparation to provide photoprotection.

29. A packaged product comprising a container, a preparation comprising a Polypodium extract and a pharmaceutically acceptable carrier for topical application within said container, and instructions for topical application of the preparation to provide photoprotection.

* * * * *